United States Patent [19]

Persson et al.

[11] 4,200,398
[45] Apr. 29, 1980

[54] AUTOMATIC VISIBILITY MEASURING SYSTEM

[75] Inventors: Anders Persson; Sven-Erik Söderström, both of Vesteras, Sweden

[73] Assignee: ASEA Aktiebolag, Vesteras, Sweden

[21] Appl. No.: 847,442

[22] Filed: Nov. 1, 1977

[30] Foreign Application Priority Data

Nov. 3, 1976 [SE] Sweden ............................... 7612218

[51] Int. Cl.$^2$ ............................................. G01N 21/22
[52] U.S. Cl. ...................................... 356/437; 250/573
[58] Field of Search ............... 356/201, 207, 436, 437, 356/438; 250/573

[56] References Cited

U.S. PATENT DOCUMENTS

| | | | |
|---|---|---|---|
| 3,393,321 | 7/1968 | Früngel | 250/573 |
| 3,694,936 | 10/1972 | Ling et al. | 250/574 |
| 3,985,452 | 10/1976 | Bylander et al. | 356/207 |

Primary Examiner—F. L. Evans
Assistant Examiner—R. A. Rosenberger
Attorney, Agent, or Firm—Watson, Cole, Grindle & Watson

[57] ABSTRACT

A visibility measuring system which comprises a radiation emitter which is capable of emitting radiation such as laser pulses in the medium in which the visibility range is to be measured, the radiation emitter being rotatable to emit the pulses in varying directions, a number of reflectors which are spaced at differing predetermined distances from the radiation emitter and laterally with respect to one another, and a radiation receiver for receiving and detecting radiation pulses reflected from each reflector; the measuring system including a device responsive to the amplitude of reflected pulses to control the direction of pulse emission from the radiation emitter to reflect from the not more than two reflectors needed to identify the current visibility range.

4 Claims, 3 Drawing Figures

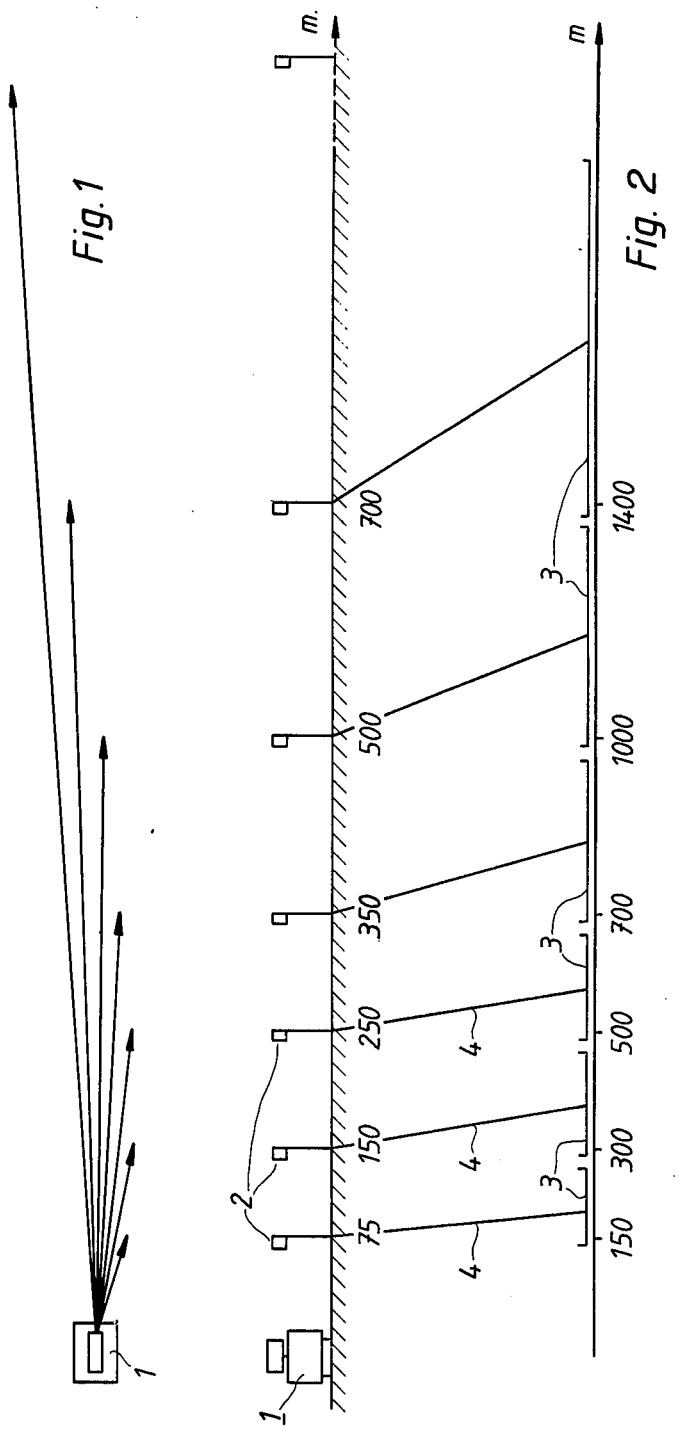

AUTOMATIC VISIBILITY MEASURING SYSTEM

BACKGROUND OF THE INVENTION

1. Field of the Invention

The present invention relates to visibility measuring systems and to improvements therein for increasing the visibility range measuring rate.

2. Description of the Prior Art

Visibility measuring systems are well known for their applicability in measuring with precision the visibility range in particular mediums at particular times and locations, and such systems have found frequent use at locations such as airfields. Different structural set-ups for such measuring systems are known, and one such set-up is shown in U.S. Pat. No. 3,694,936 wherein a radiation source is used to emit light beams towards a series of reflectors which are positioned along an essentially straight-line path from the radiation source at predetermined distances, and a receiving unit is utilized to receive the reflected beams (echoes) from the reflectors and to count the echoes which have a certain retained amplitude. By counting the number of echoes from the individual reflectors which have a certain minimum predetermined amplitude, the necessary information is obtained for determining the instantaneous distance of visibility (visibility range) in the air medium.

As is shown in U.S. patent application Ser. No. 559,049, now abandoned, an improved visibility measuring system includes a radiation source (such as a laser (light) emitter), a number of reflectors arranged at varying predetermined distances from the radiation source and with a laterally spaced-apart relationship from each other, and a receiver unit which is positioned to receive and detect reflected radiation from each individual reflector as it is sequentially illuminated by the radiation source. During the measuring cycle, each reflector is illuminated by the radiation source and the reflected radiation then measured, starting generally from the reflector located farthest from the radiation source, until all the reflectors have been illuminated. The number of reflectors which are "visible" to the receiver during the measuring cycle allows for a determination of the visibility range, this visibility range being in fact equal to twice the distance between the radiation source and the appropriately utilized reflectors (since with the receiver being attached to the radiation source, the radiation received by the receiver will have passed twice the distance between the radiation source and the reflectors).

With respect to the system in U.S. patent application Ser. No. 559,049, since the radiation source is directed towards and illuminates each reflector for a certain time interval for each measuring cycle, measurements are made with respect to all of the reflectors whether or not such is necessary to indicate the range of visibility at a particular time. Thus, if the visibility range is 500 meters at a particular time, the reflector located at a distance of 250 meters from the radiation source/receiver will be the farthest reflector from which radiation of a countable amplitude will be perceived. However, even though the reflectors then farther away will be in effect inoperable, i.e., since they will not reflect radiation sufficiently to have a countable amplitude, according to the prior art they will nevertheless be sequentially radiated during each measuring cycle, as will the nearby reflectors when (at a different time) the visibility range is quite far away. This results in the apparatus performing multiplicity of unnecessary function and thus in a reduction in the optimum visibility range measuring rate.

It is an object of the present invention to provide an improved visibility measuring system wherein the measuring rate can be increased by elimination of the unnecessary radiations and measurements of reflectance against reflectors that are irrelevant to a determination of the particular visibility range at a particular time.

SUMMARY OF THE INVENTION

According to the present invention a conventional visibility measuring system is provided with a means which is capable of eliminating the unnecessary radiation emitter operations which provide no relevant data for determining the visibility range in a particular medium at a particular time. In one embodiment the invention involves the limiting of the number of radiations of and determination of the number of reflected echoes (having a certain amplitude) from the not more than two reflectors which are needed to provide the information relevant to the determination of the current visibility range.

The invention will be further described and better understood by reference to and understanding of the accompanying drawings.

DESCRIPTION OF THE DRAWINGS

In the figures,

FIG. 1 schematically depicts the use of the inventive visibility measuring system wherein a radiation-emitting/reflection-receiver means is aimed in different angular directions;

FIG. 2 schematically depicts a side view of the relative positioning of the radiation-emitting/reflection-receiver means and the various reflectors suggested by the configuration in FIG. 1 and the visibility ranges which correspond with some of the reflectors and FIG. 3 schematically shows a block diagram of the structuring and operation of the radiation-emitting/reflection-receiver means of the invention.

DETAILED DESCRIPTION OF THE PREFERRED EMBODIMENT

Figure 3:
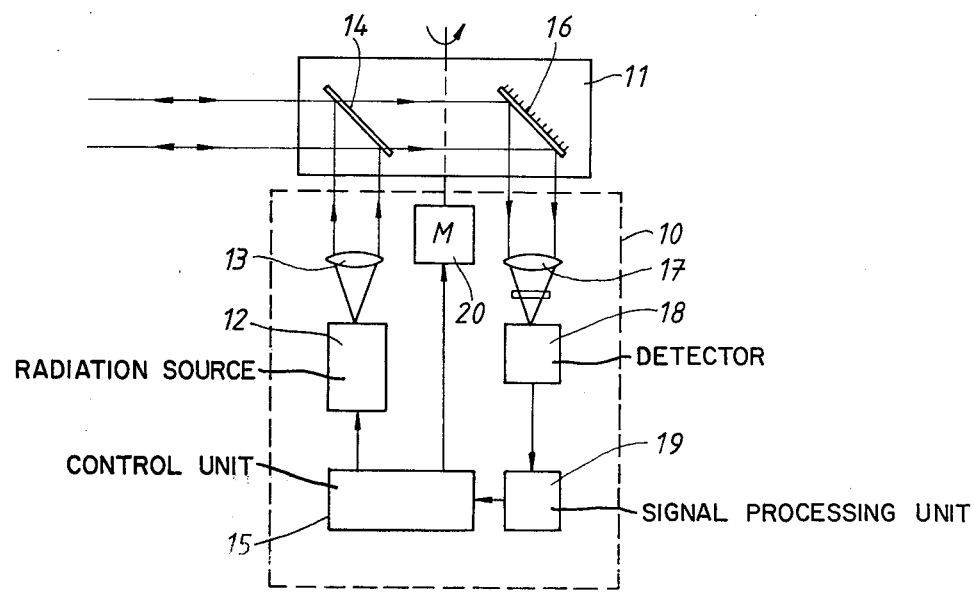

As shown in FIGS. 1 and 2, a measuring means 1, which comprises a combination radiation emitter and reflection receiver, is positioned to be capable of illuminating a number of reflectors 2 which are positioned at different predetermined distances from the measuring means, and which are located laterally of one another so that the radiation-emitter can illuminate one reflector at a time, i.e., when positioned to emit radiation at different angular orientations (FIG. 1). The illumination is carried out by emitting a number of light (laser) pulses towards each of the reflectors. Each of the reflectors is representative of a variation of visibiliy ranges as indicated by the areas 3.

According to the present invention the measuring unit is initially positioned to emit radiation towards the reflector located farthest from the radiation-emitter. If the reflected (echo) signal is of an amplitude below the level for the shortest predetermined visibility range that can be measured by means of this reflector, the measuring unit is readjusted in positioning such that the emitted radiation will be directed towards the reflector located at the second longest distance from the measuring means. If the reflected signal from this reflector is of insufficient amplitude to produce a suitable measurement in the radiation-receiver, the measuring unit is again readjusted in positioning so that emitted radiation will be directed towards the next closer reflector. This "backward stepping" continues until the particular reflector is reached which reflects the radiation sufficiently that the amplitude of the received echo is of value that the reflector can be automatically identified as the reflector as representing the area within which the visibility range is located.

Correspondingly, the measuring unit is redirected to "step forward" to reflectors located at sequentially longer distances from the measuring unit if, when taking a visibility measurement towards a certain reflector, the reflected (echo) signal has an amplitude which exceeds the predetermined signal level for the longest visibility range that can be measured by means of the reflector. In situations wherein the appropriate reflector for determining the visibility range has been determined and wherein over a period of time the visibility range remains unchanged, the measuring unit will remain unchanged in positioning so as to take measurements towards that one reflector only. In situations wherein the visibility range may lie between the areas relating to the visibility ranges determined by two adjacent reflectors, the measuring unit will take measurements alternatively towards the two "bracketing" reflectors.

The measuring unit of the invention is schematically depicted in FIG. 3 to include a radiation-emitter system 12, 13, 14 (radiation source 12, lens system 13 and semi-reflecting mirror 14), a radiation receiver system 16, 17, 18 (mirror 16, lens system 17 and detector 18), a housing 10, a housing 11, signal processing unit 19, control unit 15 and motor drive unit 20. Radiation such as laser light from means 12 is passed through lens system 13 to be directed towards the various reflectors via semi-reflecting mirror 14. The operation of radiation means 12 is controlled by control unit 15. The radiation reflected by the various illuminated reflectors reenters the housing 11 and is directed via mirror 16 to pass through lens system 17 and be detected by detector 18. Detector 18 supplies a signal to processing unit 19 which computes and presents an analogous value of the visibility. This value of the visibility is also supplied to control unit 15 which is programmed to determine whether or not drive unit 20 should be operated, and if so, whether it should be operated to rotate housing 11 to illuminate a reflector farther away from or closer to the housing 10. The stepping motor 20 is constructed so that it is capable of rotating housing 11 a certain specific angle which relates to the lateral spacing of the reflectors themselves, i.e., in an angular sense as shown in FIG. 1.

According to a different embodiment of the invention, reflectors 2 can be replaced with active light receivers which function to receive the radiation from a radiation-emitter and then transmit a signal to processing unit 19 in the housing 10. Signal processing unit 19, control unit 15, etc., then operate in essentially the same way as above when the reflectors are arranged to reflect radiation back to a radiation-emitter positioned adjacent to the radiation-emitter.

While the invention has been described in detail and with reference to specific embodiments, it will be apparent to those skilled in the art that various changes and modifications can be made therein without departing from the spirit and scope thereof.

We claim:

1. A visibility measuring system which comprises
   a means capable of emitting radiation in a multiplicity of different, predetermined directions into the medium in which the visibility is to be measured, each different, predetermined direction being representative of a different, predetermined distance from said radiation-emitting means,
   at least one means for receiving and detecting the radiation after it has been emitted from said radiation-emitting source in one of the different, predetermined directions such that it has passed through one of said different, predetermined distances in said medium, each distance representing a particular range of visibility from said radiation emitting means,
   means for automatically and continuously controlling the direction of emission of radiation into said medium from said radiation-emitting means based upon output signals from said radiation-receiver means, said direction-controlling means controlling the direction of emission of radiation so as to be stepped over to pass through a longer predetermined distance between said radiation-emitting means and said radiation-receiver means if the amplitude of radiation measured by said radiation-receiver means is higher than a certain predetermined level, to be stepped over to pass through a shorter predetermined distance between said radiation-emitting means and said radiation-receiver means if the amplitude of radiation measured by said radiation-receiver means is below a certain predetermined level, or to pass through the same predetermined distance between said radiation-emitting means and said radiation-receiver means if the amplitude of radiation measured by said radiation-receiver means is too low for stepping over to the longer predetermined distance and too high for stepping over to the shorter predetermined distance, thereby terminating further stepping of the measuring system.

2. The visibility-measuring system of claim 1, wherein a multiplicity of reflectors are spaced at different predetermined distances from said means for emitting radiation and laterally with respect to each other, each reflector corresponding with a different predetermined direction of radiation emission from said radiation-emitting means; wherein said means for receiving and detecting radiation is positioned adjacent said radiation-emitting means; wherein the radiation emitted by said radiation-emitting means is capable of being reflecting off each of said reflectors and being received by said radiation-receiver means; and wherein said means for automatically controlling the direction of radiation emitted from said radiation-emitter means includes a stepped motor capable of rotating said radiation-emitter means.

3. The visibility-measuring system of claim 2, wherein said means for automatically controlling the direction of radiation emitted from said radiation-emitter means includes a signal processing unit which receives signals from said radiation-receiver means and computes the analogous value of visibility, and a control unit which receives signals from said signal processing unit and then controls the operation of said stepped motor so as to rotate said radiation-emitter means in a direction to emit a radiation beam to a reflector located a longer predetermined distance away therefrom if the amplitude of reflected signal from one reflector is above a certain predetermined level, and to rotate said radiation-emitter means in a direction to emit a radiation beam to a reflector located closer thereto if the amplitude of reflected signal from one reflector is below a certain predetermined level.

4. The visibility-measuring system of claim 1, wherein a plurality of radiation-receiver means are spaced at different predetermined distances from said means for emitting radiation and laterally with respect to each other, each radiation-receiver means corresponding with a different predetermined direction of radiation emission from said radiation-emitting means, and wherein each radiation-receiver means is connected to said means for automatically controlling the direction of emission of radiation into said medium from said radiation-emitting means.

* * * * *